(12) United States Patent
Jia et al.

(10) Patent No.: US 7,754,873 B2
(45) Date of Patent: Jul. 13, 2010

(54) ISOLATION OF NUCLEIC ACID USING COLORED BUFFERS

(75) Inventors: Xiyu Jia, Newport Beach, CA (US); Linda Jia, Irvine, CA (US)

(73) Assignee: Zymo Research Corporation, Orange, CA (US)

( * ) Notice: Subject to any disclaimer, the term of this patent is extended or adjusted under 35 U.S.C. 154(b) by 23 days.

(21) Appl. No.: 11/205,861

(22) Filed: Aug. 16, 2005

(65) Prior Publication Data

US 2007/0015169 A1 Jan. 18, 2007

Related U.S. Application Data

(60) Provisional application No. 60/699,957, filed on Jul. 16, 2005.

(51) Int. Cl.
*C07H 21/04* (2006.01)
(52) U.S. Cl. .............. 536/25.4; 536/25.41; 536/25.42
(58) Field of Classification Search ........................ None
See application file for complete search history.

(56) References Cited

U.S. PATENT DOCUMENTS

| 5,075,430 | A | | 12/1991 | Little |
| 5,310,688 | A | * | 5/1994 | Zale et al. ............ 436/535 |
| 5,625,054 | A | | 4/1997 | Woodard |
| 5,683,916 | A | * | 11/1997 | Goffe et al. ............ 436/535 |
| 5,693,785 | A | | 12/1997 | Woodard |
| 5,808,041 | A | | 9/1998 | Padhye et al. |
| 5,922,591 | A | | 7/1999 | Anderson et al. |
| 6,281,349 | B1 | | 8/2001 | Pulleyblank |

FOREIGN PATENT DOCUMENTS

| WO | WO95/04756 A1 * | 2/1995 |
| WO | WO00/06601 A1 * | 2/2000 |
| WO | WO2004/106516 A1 * | 12/2004 |

OTHER PUBLICATIONS

[R] Emanuel, J., "Phase Lock Gel Plasmid Micropreps: Direct Insert Screening, Probe Synthesis and Sequencing Within One Day," Nucleic Acids Research, 20(3), 625 (1992).*

(S) Clewell et al., "Supercoiled Circular DNA-Protein Complex in *Escherichia Coli*: Purification and Induced Conversion to an Open Circular DNA Form," Proc. National Academy Sciences USA, 62(4), 1159-1166 (Apr. 15, 1969).*
Clewell and Helsenki, Properties of Deoxyribonucleic Acid-Protein Relaxation COmplex, 1970, Biochemistry, V.9, No. 22, 4428-4440.
Birnboim and Dolly, A rapid alkaline extraction procedure for screening recombinant plasmid DNA, 1979, N.A.R., V.7 No. 6, 1513-1523.
Volgelstein and Gillespie, Preparation and analytical purification of DNA from agarose, 1979, P.N.A.S., V. 76, No. 2, 615-619.
Holmes and Quigley, A RApid Boiling Method for the Preperation of Bacterial PLasmids, 1981, Analytical Biochemistry, 114, 193-197.
Marko et al., A Procedure for the LArge-Scale Isolation of Highly Purified Plasmid DNA Using Alkaline Extraction . . . , 1982, Analytical Biochemistry, 121, 382-387.
Birnboim, 1983, Methods in Enzymology, A Rapid Alkaline etraction Method for the Isolation of Plasmid DNA, 1983, V. 100, 243-255.
Sambrook and Russell, Chapter 1, Protocol 9: Purification of Plasmid DNA by Chromatography, 2000, Cold Spring Harbor Laboratory Press.
Sambrook and Russell, Chapter 1, Protocol 1: Preperation of Plasmid DNA by Alkaline Lysis with SDS: Minipreperation, 2000, Cold Spring Harbor Laboratory Press.

* cited by examiner

*Primary Examiner*—Lawrence E Crane
(74) *Attorney, Agent, or Firm*—Jonathan A. Claypool

(57) ABSTRACT

The present invention describes isolation of plasmid DNA from bacteria. The addition of dyes to the alkaline lysis based purification buffers (P1, P2, and P3) allows for improved visual monitoring of the steps of preparing a bacterial lysate filtrate coupled to filtration or spin-column chromatography. The method comprises the suspending of the bacterial cells with buffer P1 (suspension is red/pink); lysing the bacteria with buffer P2 (suspension goes from red/purple color to translucent/purple); precipitating cellular debris with buffer P3 (solution becomes yellow with debris suspension); centrifuging or filtering to product a lysate filtrate; binding the lysate filtrate to a DNA binding matrix; washing; and isolating the plasmid via chromatography. The yield and quality of plasmid DNA is improved due to more consistent lysis. Errors in buffer addition are reduced by visualizing the color as buffers are added and also of changes in color of the preparation at each step.

29 Claims, 5 Drawing Sheets

Example 1
Spin–Column:
~25 ul elution volume

Example 2
Spin–Column:
~40 ul elution volume

Plasmid DNA

ISOLATION OF NUCLEIC ACID USING COLORED BUFFERS

CROSS REFERENCE TO RELATED APPLICATIONS

This application claims priority to U.S. provisional application 60/699,957 filed Jul. 16, 2005.

BACKGROUND OF THE INVENTION

1. Field of the Invention

The present invention relates to isolating pure plasmid DNA from *E. coli* and other organisms. The addition of indicator dyes to the alkaline lysis based buffers allows for easy and rapid visual monitoring of the resuspension, lysis, and neutralization steps. The ability to assess the process increases plasmid yield and also reduces errors. The present invention is useful in other nucleic acid purification applications.

2. Description of the Related Art

The present invention relates to the purification of plasmid DNA and other nucleic acids from source materials. The purification of plasmid DNA from bacterial lysates is a standard molecular biological technique that is critical for downstream recombinant DNA manipulations. It is critical and consumes significant resources of academicians and scientists in biotechnology research and development. The purity and quantity of the plasmid DNA are important factors that remain troublesome for the entire scientific community. The sensitive reactions commonly employed in molecular biology experiments of reverse transcription, transcription, DNA and RNA sequencing, polymerase chain reaction (PCR), restriction digests, ligation reactions, end modifications, among other similar based modification procedures require the plasmid DNA, or other nucleic acid molecules be free from contaminants. It is also desirable to isolate the nucleic acid in significant quantities to ensure a reliable source of material with which to proceed to additional experiments. In many instances there is a need to move a desired plasmid DNA, or fragment thereof, through several manipulations to reach the desired endpoint. Cloning procedures are often complex and involve numerous steps and so methods that reliably isolate pure plasmid DNA, and other nucleic acids, in significant quantities are desired. Contaminants are and remain a persistent problem and the majority of them often result from the initial steps of lysis of the bacteria through clearing of the lysate. In addition, the lysis and neutralization, or clearing steps, are often the points where significant loss of the desired plasmid DNA, or nucleic acid, is encountered.

Conventional procedures for isolating plasmid DNA includes harvesting the bacterial cells and obtaining the plasmid DNA, or other target nucleic acid, in a pure form via lysis, free from the undesirable contaminating medium and the cellular constituents. This is typically called a cleared bacterial or cellular lysate. The cell lysis may be performed in a variety of ways including mechanical sonication or blending, enzymatic digestion and also the traditional chemical means of alkaline lysis. The alkaline lysis based protocols remain the basis for many plasmid purification methods, though other procedures such as the boiling lysis, triton lysis, polyethylene glycol protocols are also used (Bimboim and Dolly, 1979 Nucl. Acids Res. 7:1513-1523; H. Bimboim, 1983, Meth. in Enzym., vol. 100, pp. 243-255, Holmes and Quigley, 1981, Anal. Biochem. 114:193-197; Clewell and Helinski, 1970, Biochemistry, 9:4428-4440; Lis and Schleif, 1975 Nucl. Acids Res. 2:757). The dominant alkaline lysis method's lysis and neutralization steps are important points where loss is observed and cellular contaminants are introduced, often unnecessarily.

Approaches that coupled alkaline lysis to cesium chloride gradient centrifugation and organic extraction with toxic and caustic phenol/chloroform and alcohols have largely been replaced by a variety of systems that utilize coupling a cleared lysate to rapid and efficient chromatographic methods. The observation that DNA bound preferentially to ground glass or glass fiber disks in the presence of high concentrations of sodium iodide or sodium perchlorate has allowed the development of new purification methodology based on these results (Marko et al. 1981, Analyt. Biochem. 121:382-387, Vogelstein et al. 1979, Proc. Nat. Acad. Sci. 76:615-619). The use of the chaotropic salt solutions such as guanidinium, iodide, perchlortate, and trichloroacetate coupled to forms of silica based or other chromatographic techniques, has resulted in a preferred methodology for plasmid as well as general nucleic acid purification.

These systems often employ the use of such chaotropic salts together with chromatographic techniques either in small or large scale formats that are typically based on the silica based materials of diatomaceous earth, silica particles, silica resins, silica embedded filters, magnetic silica particles, and different combinations thereof. In addition modified silica materials and ion exchange resins are also commonly used, either alone or in combinations in the form of hybrid resins. Additionally other chromatographic techniques have been commonly used in nucleic acid purification procedures. Despite these improvements and the development of numerous systems based on these technologies there remains a need to develop improved systems to satisfy demands for easier, faster protocols with increased yield and reliability for high-level quantity purification of plasmids and other nucleic acid materials.

Generally, the plasmid or nucleic acid is bound to the matrix using vacuum filtration or centrifugation methods, washed on the column similarly and finally eluted with water, TE buffer, or other elution buffer. Many preparations have been developed commercially, such as the Wizard.™ DNA purification line of products (Promega Corporation); or the Qiagen line of DNA isolation systems from. (Qiagen Corp.), the FlexiPrep (Pharmiacia), and GeniePrep (Ambion), among others.

All of these commercial procedures do not adequately address the formation of the cleared lysate from which the plasmid, or nucleic acid, is to be purified. The commercial market for plasmid purification has developed to a multimillion dollar industry, but has focused largely on the final chromatographic purification steps. Thus most of the advances in plasmid purification ignore the early steps of nucleic acid isolation that are crucial for the yield and quality of the isolated product.

The means of preparing a cleared bacterial, or other biological source of lysate, is a point that has remained problematic and overlooked. Ensuring that complete lysis and neutralization occurs can be more important for yield and also for eliminating contaminants, than the later chromatographic steps. Quite often inefficient lysis and neutralization leads to contaminants being carried over into later steps and dramatic reduction in yield. Advances in these early steps in plasmid and nucleic acid purification procedures will ensure that the significant improvements and modifications in silica matrixes, particles, and chromatographic procedures, have cleaner and more abundant starting material. Other problems associated with many current techniques are inefficient sample handling, overall time delay, and reduced yields.

Improved visual recognition of lysis would improve overall quality and yield, especially when the nucleic acid in question is in low supply due to intrinsic factors such as low copy number, toxicity, or limited availability of the starting biological material.

SUMMARY OF THE INVENTION

The present invention provides a fast, reliable, and efficient method for the isolation of pure plasmid DNA based on a modified alkaline lysis procedure. The present invention ensures optimization of the bacterial lysis and neutralization steps by visualization of color changes due to indicator dyes present in the individual buffers that can reflect the pH of the solution after mixing (FIG. 1). In a preferred embodiment the color change is based on indicator dyes whose color is related to the pH of the solution and allows the efficiency of lysis and neutralization, and clearing of the lysate, to be assessed visually. In other embodiments the indicator is different in each of the buffers and may not undergo a response to pH. The presence of one or more indicator dyes also guards against accidental errors in sample handling related to pipeting of the resuspension buffer, lysis buffer, and neutralization buffer, or any buffer component. It also allows one to determine if the removal of the media supernatant is complete. Furthermore, since it is easy to gauge the degree of lysis and neutralization by simply examining the color changes by eye one is confident that the manipulations are complete and successful (FIG. 2). It is common for poor execution of these basic processes to result in inferior nucleic acid products. The preferred embodiment provides a process that increases the quality and yield of plasmid DNA, or other nucleic acid isolated, in small elution volume. The format of the present invention is preferentially coupled to chromatography, preferentially spin-column based (FIG. 3). A preferred embodiment uses silica based chromatography that allows for elution into small volumes of water, TE, or elution buffer. However, other forms of chromatography are also contemplated. The resulting plasmid DNA, or nucleic acid, is suitable for any molecular biological application, including, transfection, sequencing, transcriptions, ligations, cloning, among others sensitive applications (FIGS. 4, 5). The stability of plasmids isolated by this novel method is enough that they may be stored for prolonged times at room temperature. It is also recognized that specific embodiments of this invention can be adapted for isolation of any nucleic acid from a variety of sources.

The presence of the indicator dyes allows the pH, or other aspect of the lysate to be monitored visually and ensures that the lysis and neutralization steps are complete. This process optimizes the lysate in regards to the amount and purity of plasmid, for processing in later purification steps. It also saves valuable time and reduces errors of sample handling. The mixing of the colored buffers offers an easy visual monitoring of each step of these processes. The standard alkaline lysis purification method employs typically three buffers, though a single buffer format is an alternative embodiment of the present invention. In a preferred embodiment, the first resuspension buffer is around neutral pH, red in color, and preferentially contains the indicator dye, phenol red, though other similar dyes, or indicators can be used (FIG. 1). The second is basic and blue in color, containing the dye emerald green or similar dye, or indicator (FIG. 1). The third buffer is acidic and yellow in color, also contains phenol red, or a similar dye or indicator and is a different color from the first and second buffer (FIG. 1). Preferred dyes or indicators for use are ones that display different color ranges in the pH range suitable for plasmid DNA isolation (about pH 2.5-5.5), or have properties that allow visual monitoring of the bacterial lysate. Each step can easily be visually monitored ensuring optimal lysis and neutralization and the highest quality cleared lysate. Lysates may be cleared by centrifugation or filtration both of which are known in the art.

The cleared lysate is then preferably subjected to silica based column chromatography, or similar chromatographic methods known in the art, to further purify the plasmid, or other nucleic acid, which is finally eluted into a small volume of water, TE, or other elution buffer (FIG. 2). The purified plasmid DNA is pure and suitable for sensitive molecular biology based experiments (FIGS. 3, 4).

BRIEF DESCRIPTION OF THE DRAWINGS

A detailed description of the preferred embodiments is provided herein below with reference to the following drawings.

DETAILED DESCRIPTION OF THE PREFERRED EMBODIMENTS

The following description is of the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

The present invention provides a fast, reliable, and efficient method for the isolation of pure plasmid DNA, or other nucleic acids, in a format that is coupled to silica based or other chromatographic methods that allows the plasmid, or nucleic acid, to be eluted in small volumes. The addition of colored dyes, or other indicators, to buffers used to make the cleared lysate allows the process to be visually monitored. In specific embodiments employing modified alkaline lysis based buffers the neutralization of the second basic buffer (sodium hydroxide, NaOH/SDS) can also be monitored. The resulting plasmid DNA or nucleic acid is pure and suitable for use in sensitive molecular biology applications, such as reverse transcription, transcription, DNA and RNA sequencing, polymerase chain reaction (PCR), restriction digests, ligation reactions, end modifications, among other procedures. In the case of plasmid DNA it is pure to be stable at room temperature for prolonged time. The different embodiments of the invention provide for small scale purification to larger preparations designed to purify significant quantities of plasmid or nucleic acid material from a variety of sources.

Nucleic acids and specifically plasmid DNA can be isolated from microbial fermentation and/or eukaryotic cellular cultures. The plasmid DNA can be preferentially isolated from *Escherichia coli* (*E. coli*) strains that are usually used to product such material for most molecular biology manipulations. It is recognized that other prokaryotic bacterial or eukaryotic species can also be utilized as vehicles for the purification of nucleic acids or plasmid DNA. The nucleic acid to be purified is typically plasmid DNA of a variety of sizes, but could be RNA, or genomic DNA in alternative embodiments. In the case of plasmid DNA it may or may not contain foreign DNA sequence.

The cellular culture can be grown in a variety of culture mediums that can be modified to alter or regulate replication of the plasmid DNA, RNA, or other nucleic acid molecules. The cells are harvested by centrifugation and the culture media removed to provide a cell pellet. In a preferred embodiment the nucleic acid that is isolated is plasmid DNA that can be of a variety of sizes with specific control elements that, either containing heterologous DNA or synthetic sequences that are commonly known in the art.

Figure 1:
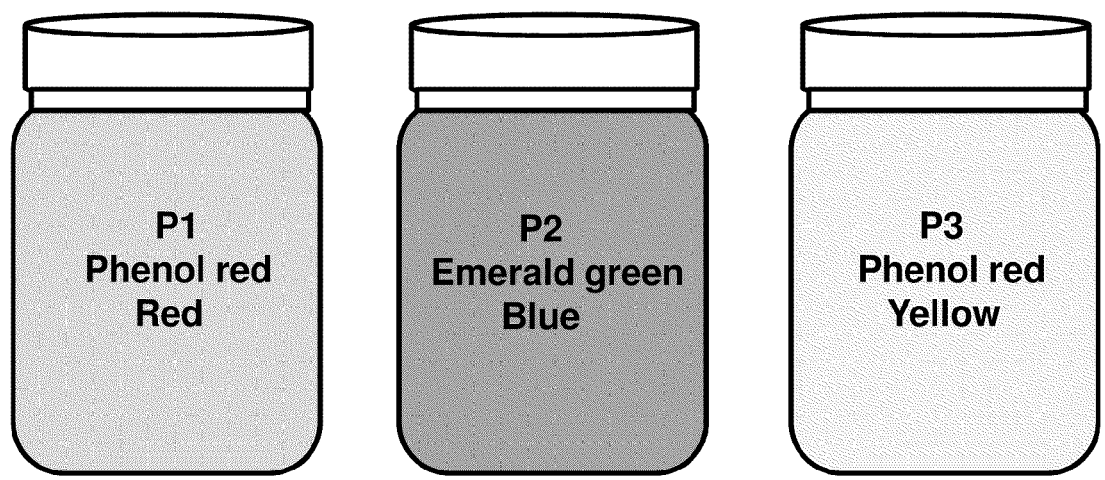
FIG. 1. Colored alkaline lysis based buffers containing indicator dyes used in the plasmid isolation (P1 (red, Phenol Red), P2 (blue, Emerald Green), and P3 (yellow, Phenol Red) are shown.
Figure 2:
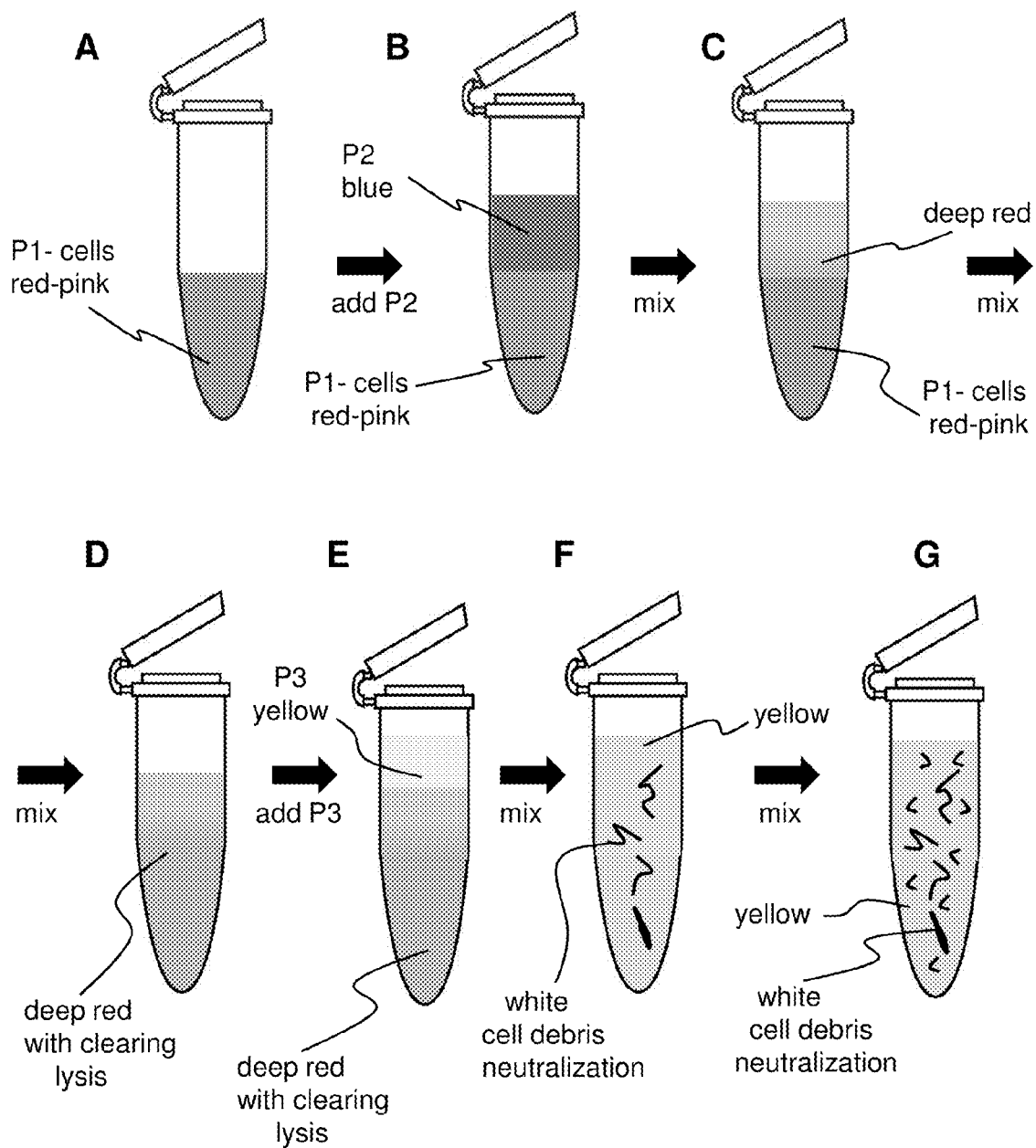
FIG. 2. A.-G: A. The bacterial pellet is shown resuspended in alkaline lysis buffer P1 (red). The red color is evident. B-D. The addition of buffer P2 (blue) results in a change in the color and complete lysis of the bacteria. D-G. The addition of the neutralization buffer P3 (yellow) results is a second color change and the precipitation of the cellular material in a neutralized lysate.

The present invention incorporates the addition of dyes, or other indicators, to the nucleic acid isolation buffers (FIG. 1). The dye can be present in amounts and with intrinsic characteristics such that it provides enough color for monitoring, but does not alter other characteristics of the cellular lysates, plasmid DNA, purified nucleic acids, or remain after the final chromatographic purification (FIG. 2). Numerous chromatographic methods are known in the art and are commercially available from a variety of sources. Many of these are compatible with the preferred embodiments of the present invention and allow final purification of the plasmid DNA, or nucleic acid from the cleared lysate. There are numerous commercially available candidate dyes or indicators that are contemplated for use including, but not limited to pH indicator dyes, reactive dyes, direct dyes, sulfur dyes, cationic dyes, anionic dyes, intercalating dyes, nucleic acid dyes, and metal complex dyes, among other specific dyes known to those skilled in the art. The indicator dyes are useful due to their property to change color in relation to the pH of the solution. However, many additional dyes or indicators are known in the art and can be used in embodiments of the present invention that are not pH responsive. These can be used alone or in combination with other dyes or indicators to monitor the status of the cellular lysate from which nucleic acids are being purified. In the preferred embodiment of the present invention the color of the cellular lysates is easily followed by simple color transitions by eye due to the presence of the component dyes. These can be different in each of the alkaline lysis based buffers. In other embodiments, a spectrophotometer or like methods is used to assay changes in the cellular lysates.

In one preferred embodiment the pH indicator dye phenol red can be used. Phenol red is commercially available in several formats or compositions and has a visual transition interval of yellow at about pH 6.8 to red are pH of about 8.4, with a transition range of between about pH 6.5-pH 8.5. The phenol red is added to the alkaline lysis buffer P1 (around neutral pH 7.0-8.0 and red in color) and P3 (acidic and yellow in color), while another dye such as emerald-green (blue) is added to the P2 (basic and blue-green in color) (FIG. 1). This preferred embodiment allows for easy and efficient visual monitoring of the steps of clearing the bacterial lysate. One feature of the present invention is the probability of one making errors is reduced due to the ability to easily see the changes in the lysate as each of the buffers is added sequentially.

Other similar dyes that undergo color transitions in relation to pH, binding, or due to other parameters, are known in the art and are also alternative embodiments of the invention. Other commercially available dyes useful in embodiments of the present invention include, but are not limited to, chloro phenol red (Sigma); emerald green (Alza); methyl red (Sigma); methyl green; (Sigma); thymol blue (Sigma); bromo thymol blue (Sigma); o-cresolphthalein (Nile); meta cresol purple (Nile); thymolphthalein (Nile); phenolphthalein (Nile); titan yellow (Sigma); xylene cyanol; methyl orange (Sigma);

neutral red (Sigma); cresol red (Sigma); bromo cresol blue (Sigma); bromo cresol green (Sigma); bromo cresol purple (Sigma); methylene blue (Sigma); bromo phenol blue (Sigma), indigo carmine (Aldrich); methyl viologen dichloride; resorufin (Aldrich); resazurin (Aldrich); phenosafranine (Aldrich); carboxyfluorescein (molecular probes); napthtofluorescein (Molecular probes); Oregon green (Molecular probes); SNAFL-1 (Molecular probes); SNARF-1 (Molecular probes); 6-TET (Molecular probes), among other similar dyes, and combinations thereof. In addition dyes can be used either alone or in combinations to allow easy visual or spectrophotometric monitoring of the cellular lysates or solutions. In preferred embodiments of the present invention dyes that are non toxic or those with low toxicity can be used.

Plasmid Purification

Inoculums of *E. coli* from a single bacterial colony are grown to saturation (overnight), or to the desired cellular density. Media can be any of the commonly used for bacterial cultures such as luria broth, terrific broth, super broth, among other suitable culture media known in the art. The chromatographic purification procedures are preferentially carried out at room temperature and are known in the art. All centrifugation steps are performed at a speed pf about 11,000-14,000 rpm in a standard laboratory microcentrifuge.

Figure 3:
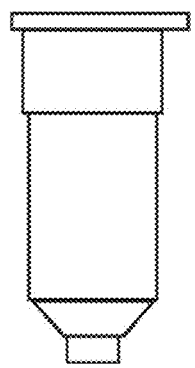
FIG. 3. Spin-columns used in embodiments of the present invention are shown.
Figure 3:
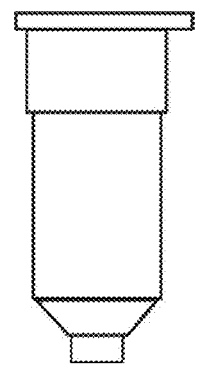
Figure 4:
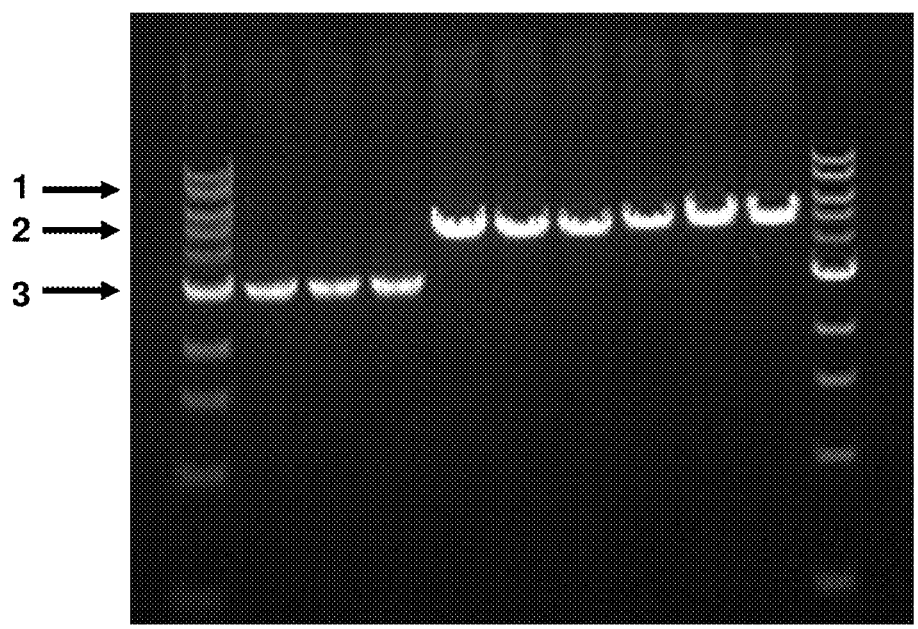
FIG. 4. A one percent agarose gel, shows the purification of three different sized plasmids purified from *E. coli* (3.0 kb, 5.0 kb, and 5.5 kb, loaded in triplicate).
Figure 5:
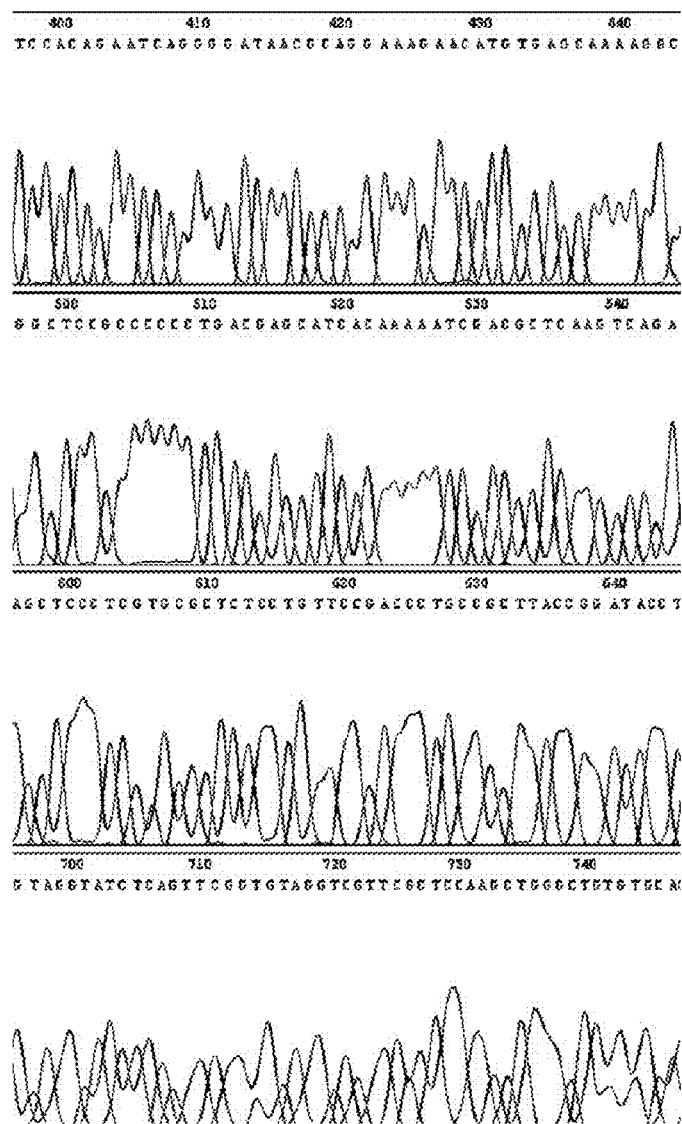
FIG. 5. A sequence trace from a standard sequencing reaction of a representative plasmid DNA isolated using the preferred embodiment of the present invention is shown (Example 1).

The isolation of plasmid DNA is a preferred embodiment of the present invention. All steps of the preferred embodiment of the present invention may be carried out at room temperature, about 15-30° C. Isolation of plasmid DNA is well known in the art. The method of plasmid isolation comprises modified mild alkaline lysis of host cells containing a plasmid, sodium hydroxide (NaOH) and sodium dodecyl sulphate (SDS), NaOH/SDS, denaturation, and precipitation of unwanted cellular macromolecular components as an insoluble precipitate, coupled to column based silica, or other chromatography or purification methods. This procedure is modified from the original alkaline lysis plasmid preparation procedure and utilizes reduced NaOH (less than 0.2 M) to allow the lysis to be performed at room temperature and also uses guanidine as a denaturant. Isolation buffers based on alkaline lysis protocols are well known in the art and variations of compositions are contemplated as embodiments of the present invention that are compatible with various commercially available chromatographic columns and technologies. Alkaline lysis procedures use sodium acetate, potassium acetate, as well as a variety of other salts, including chaotropic salts such as iodine and guanidine, among others known in the art. The ribonuclease RNAase A is commonly added in some protocols to degrade contaminating RNA from the lysate. The colored buffer system can be used with all variations and simplifies sample manipulation and prevents errors (FIG. 1). The visual monitoring increases efficiency and significantly reduces the time required to process each sample. Plasmid can be isolated, typically up to about 25 ug from 1.5 ml of standard *E. coli* starting material and after purification on silica based spin-columns (FIG. 2). The plasmid is pure typically with an $OD_{260/280}$ ratio above 1.8. The plasmid DNA is suitably pure for use in the most sensitive experiments (FIGS. 2, 3, 4).

Alkaline Lysis Based Colored Buffers for Plasmid Nucleic Acid Purification

Preferred embodiment and alternative embodiments have different dyes, indicators, or salts, or component chemical components and or concentrations. The below example buffers are embodiments of the present invention and others are contemplated. The colored buffer system simplifies protocol manipulation and prevents errors. Various molecular biology and biochemical methods, media components, or other items concerning plasmid isolation mentioned, but not explicitly described in this disclosure are commonly known in the scientific literature and to one skilled in the art. The examples detailed are for small minipreperation of plasmid samples from *E. coli* from standard overnight cultures.

Alkaline Lysis Based Buffers:
1. Buffer P1: Resuspension Buffer, color red.

Final Concentration:
    50 mM Tris-HCl, pH 8.0.
    mM EDTA, pH 8.0.
    ~0.05 mM Phenol Red (about 20 mg indicator dye per liter, Disodium salt).
    ~100 ug/ml RNAse A (added before use, store at 4° C.).
2. Buffer P2: Lysis Buffer, color blue.

Final Concentration:
    ~1.0% SDS (sodium dodecyl sulfate).
    175 mM NaOH (sodium hygdroxide).
    ~0.10 mM Emerald green (about 40 mg indicator dye per liter, Disodium salt).
3. Buffer P3: Neutralization Buffer, color yellow.

Final Concentration:
    3.0 M KOAc, pH 5.5 (3 M potassium, 5M acetate)
    ~70-100 mM guanidine (guanidine hydrochloride, or other chaotropic salt)
    ~0.05 mM Phenol Red (about 20 mg indicator dye per liter, Disodium salt)
4. Wash Buffer: 70-80% ethanol, or other organic solvent based buffer. Many wash buffers are compatible with the present invention and are commonly known in the art.

EXAMPLES OF PLASMID PURIFICATION

Separate cultures of *E. coli* strain JM109 containing plasmids of different sizes (3.0 kb, 5.0 kb, and 5.5 kb) were grown to saturation at 37.degree. C. overnight with shaking in an incubator (New Brunswick). The following example protocols were used to isolate plasmid DNA using the modified alkaline lysis based buffers described above. Once the cleared bacterial lysate was made this was further purified over silica based spin-columns (FIG. 2; example 1 and 2) (Zymo Research Corp). The clarification of the lysate can be performed by centrifugation or filtration methods both of which are known in the art. Some protocols utilize lysozyme, while others dispense with this step. The pure plasmid was suitable for sensitive molecular biology techniques and representative samples isolated via the protocol of example 1 are shown (FIG. 3). The typical ratio OD.sub.260/280 is above 1.8 with yields up to 25 ug per ml of bacterial culture. The plasmid DNA was sequenced using standard Sanger dideoxy techniques and a representative sequence trace is shown (FIG. 4) (Gibco). The lysates were also purified on alternate spin-columns that are suitable for either use in a microfuge (Eppendorf) or vacuum manifold (Example 2).

In addition such lysates are suitable to scale up for use in large scale methods for use with mid to large sized cultures from about 10 ml to several liters, or larger cultures of about 500 ml, or industrial sized cultures using fermentation equipment known in the art and are all embodiments of the present invention (2001 Sambrook and Russell, 2001). Additional embodiments of the invention are suitable for high through put multiple sample analysis (See example 3).

Example 1

Preferred Embodiment

Spin-Column (Modified Low Volume Elution)

1. Pellet 0.5-5 ml of overnight culture in a 1.5 ml microfuge tube by spinning for 15-20 seconds.
2. Discard the supernatant.
3. Add 200 ul of P1 buffer (red), containing RNAse A (100 ug/ml). Resuspend completely with gentle vortexing or by pipette. Solution is pink or light red in color to the naked eye.
4. Add 200 ul of P2 buffer (blue). Mix by inverting and swirling the microfuge tube 4-6 about times. The solution becomes clear and a deeper red in color. If lysis is incomplete the clearing and darkening to a red of the color is qualitatively less pronounced to the naked eye.
5. Add 400 ul pf P3 buffer (yellow) and mix thoroughly, but gently. Do not vortex this step hard. A white precipitate will form which consists of K-SDS and cellular debris. The buffer becomes yellow and cleared debris suspension.
6. Spin the microfuge tube for 3 minutes at maximum speed.
7. Load the supernatant intro a spin-column (various types are commercially available.). This may be done by pouring or pipette. Be careful not to transfer or disturb any of the white cellular precipitate.
8. Spin the spin-column with the collection tube for 30 seconds.
9. Discard the flow-through in the collection tube. Make sure the flow-through does not touch the bottom part of the column as it would contaminate the DNA inside the column.
10. Add 600 ul of Wash Buffer onto the column with the collection tube and spin for 30 seconds.
11. Add about 25 ul (low volume) of Elution Buffer to the column and place the column onto a 1.5 ml microfuge tube, spin for 10-15 seconds to elute the plasmid DNA. Elution Buffer contains 10 mM Tris.HCl, pH 8.5, 0.1 mM EDTA. Pure water can also be used for elution if needed. Dispense the Elution Buffer directly onto the center of the spin column membrane for an optimal plasmid elution.

Example 2

Preferred Embodiment

Spin-Column (Standard: Microfuge or Vacuum Elution)

1. Pellet 0.5-5 ml of overnight culture in a 1.5 ml microfuge tube by spinning for 15-20 seconds.
2. Discard the supernatant.
3. Add 200 ul of P1 buffer (red). Resuspend completely with gentle vortexing or by pipette. Solution becomes pink or light red in color to the naked eye.

4. Add 200 ul of P2 buffer (blue). Mix by inverting and swirling the microfuge tube 4-6 about times. The solution becomes clear and a deeper red in color. If lysis is incomplete the clearing and darkening to a red of the color is qualitatively less pronounced to the naked eye.
5. Add 400 ul pf P3 buffer (yellow) and mix thoroughly, but gently. Do not vortex this step hard. A white precipitate will form which consists of K-SDS and cellular debris. Shaking the tube inverted several times increases the efficiency of precipitate formation.
6. Spin microfuge tube for 3 minutes.
7. Load the supernatant intro a spin-column (various types are commercially available.). This may be done by pouring or pipette. Be careful not to transfer or disturb any of the white cellular precipitate.
8. Spin the spin-column with the collection tube for 30 seconds.
9. Discard the flow-through in the collection tube. Make sure the flow-through does not touch the bottom part of the column as it would contaminate the DNA inside the column.
10. Add 600 ul of Wash Buffer onto the column with the collection tube and spin for 30 seconds.
11. Add about 40 ul of Elution Buffer to the column and place the column onto a 1.5 ml microfuge tube, spin for 10-15 seconds to elute the plasmid. Elution Buffer contains 10 mM Tris.HCl, pH 8.5, 0.1 mM EDTA. Pure water can also be used for elution if needed. Dispense the Elution Buffer directly onto the center of the spin column membrane for an optimal plasmid elution (can use commercially available vacuum manifold apparatus as an alternative).

Example 3

Short Procedure

Alternative Embodiment

1. Pellet 0.5-5 ml of overnight culture. Discard supernatant.
2. Add 200 ul of P1 buffer (red) and resuspend pellet, becomes light red or pink.
3. Add 200 ul of P2 buffer (blue) and mix, becomes deeper red and clear to the naked eye.
4. Add 400 ul of P3 buffer (yellow) and mix thoroughly, white cellular precipitate forms.
5. Spin full speed for 3 minutes.
6. Load supernatant to the spin-column.
7. Spin the column with the collection tube for 30 sec.
8. Discard the flow-through.
9. Add 600 ul of Wash buffer and spin for 30 sec.
10. Add 40 ul (25 ul) of Elution Buffer or water, put the column into a new microfuge tube, and spin for 10 sec.

Example 4

Alternative Embodiment

96 Well or Larger Format

The present invention is compatible with a 96 well or larger number sample format for high throughput sample analysis as an alternative embodiment. The amounts of samples, buffers, and manipulations for high through-put sample handling as well as optimal centrifugation speeds are well known in the art. The 96 well plates and larger number sample plates that are compatible with robotic methods are known in the art and are readily commercially available.

Example 5

Source Material from Other Species

Yeast species, fungi species, other microorganisms, *Homo sapiens* (human) liquid tissue, *Homo sapiens* (human) solid tissue, or tissue from a variety of species commonly used in diagnostic, research or clinical laboratories are contemplated as compatible with this purification procedure as a source of plasmid DNA are all alternative embodiments of the present invention. Procedures for handling and preparing samples from these various species are well known in the art and are reported in the scientific literature.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described.

REFERENCES

Molecular Cloning A laboratory Manual, Third Edition, 2001, Joseph Sambrook and David W. Russell, Cold Spring Harbor Laboratory Press, Cold Spring Harbor N.Y.
Bimboim and Dolly, 1979 Nucl. Acids Res. 7:1513-1523.
H. Bimboim, 1983, Meth. in Enzym., vol. 100, pp. 243-255.
Holmes and Quigley, 1981, Anal. Biochem. 114:193-197.
Clewell and Helinski, 1970, Biochemistry, 9:4428-4440.
Lis and Schleif, 1975 Nucl. Acids Res. 2:757.
Marko et al. 1981, Analyt. Biochem. 121:382-387.
Vogelstein et al. 1979, Proc. Nat. Acad. Sci. 76:615-619.

What is claimed is:

1. A method for isolating plasmid DNA from bacteria via alkaline lysis, the method comprising:
   (a) suspending bacterial cells in a P1 buffer with a pH of between 7-9; wherein the P1 buffer contains a dye for monitoring suspension of the bacterial cells, whereby adding the P1 buffer results in a colored bacterial suspension allowing visual inspection of the colored bacterial suspension ensuring efficient suspension of the bacteria from added contrast resulting from the colored bacterial suspension;
   (b) adding a sufficient amount of P2 buffer with a basic pH of between 11-14 to the bacterial suspension, wherein the P2 buffer contains a dye for monitoring the lysis of the bacterial suspension, whereby adding and mixing the P2 buffer to the bacterial suspension results in efficient lysis producing a bacterial lysate and wherein the color of the lysate changes and clarifies indicating that lysis of the bacterial suspension is complete and that the P2 buffer was effective in causing efficient lysis;
   (c) precipitating cellular debris by adding a sufficient amount of P3 neutralization buffer with a pH of between 3-6 producing a cleared bacterial lysate containing increased amounts plasmid DNA due to the efficient neutralization; wherein the P3 buffer contains a dye; and wherein the color of the cleared bacterial lysate changes upon adding the P3 buffer indicating the P3 buffer was effective in causing efficient neutralization;
   (d) removing cellular debris from the cleared bacterial lysate by filtering or centrifuging to obtain a lysate filtrate, and then adsorbing the plasmid DNA in the lysate by passing the lysate filtrate over a DNA binding matrix, whereby the dye or dyes in the colored cleared lysate passes or pass through the DNA binding matrix and thereby is or are discarded as part of the waste flow through;
   (e) washing the adsorbed plasmid DNA on the DNA binding matrix by adding wash buffer and filtering or centrifuging to obtain a clear flow through of wash buffer, discarding the clear flow through wash buffer; and
   (f) eluting the plasmid DNA from the DNA binding matrix by adding an elution buffer and filtering or centrifuging to obtain a plasmid DNA containing eluate.

2. The method of claim 1 wherein the sole dye in the P1 buffer, P2 buffer, and P3 buffer is an indicator dye or other similar dye wherein solutions of said dye change color at within the pH range of about 6 to about 8.

3. The method of claim 1 wherein each of the buffers P1, P2, and P3 contain a different dye.

4. The method of claim 1 wherein the dyes are indicator dyes or other similar dyes that are selected from the group consisting of: phenol red; emerald green; and methylene blue.

5. The method of claim 1 wherein each of the buffers P1, P2, and P3 contain the same dye.

6. The method of claim 5 wherein the dye selected is the indicator phenol red.

7. The method of claim 1 further comprising deletion of the step where the P1 buffer is added, and wherein the bacterial cells to be lysed are added directly to the P2 buffer as the initial process step.

8. The method of claim 1 wherein the DNA binding matrix is silica based.

9. The method of claim 1 wherein the dye selected to be in buffers P1 and P3 is the indicator phenol red and the dye selected to be in buffer P2 is a different dye.

10. The method of claim 1 wherein the buffers P1, P2, or P3 each further comprises an additional indicator dye or other similar dye.

11. A method for isolating plasmid DNA from bacteria via alkaline lysis, the method comprising:
   (a) suspending bacterial cells in a P1 buffer with a pH of between 7-9; wherein the P1 buffer contains an indicator dye for monitoring suspension of the bacterial cells, wherein adding the P1 buffer results in a colored bacterial suspension allowing visual inspection of the colored bacterial suspension to ensure efficient suspension of the bacteria by observation of the added contrast resulting from the colored bacterial suspension;
   (b) adding a sufficient amount of P2 buffer with a basic pH of between 11-14 to the bacterial suspension, wherein the P2 buffer contains an indicator dye for monitoring the lysis of the bacterial suspension, whereby adding and mixing the P2 buffer to the bacterial suspension results in efficient lysis producing a bacterial lysate and wherein a visible color change results from the increase in pH; and wherein the clarification of the colored bacterial lysate indicates that lysis of the bacterial suspension is complete and that the P2 buffer was effective in causing efficient lysis;
   (c) precipitating cellular debris by adding a sufficient amount of P3 neutralization buffer with a pH of between 3-6 producing a cleared bacterial lysate containing increased amounts plasmid DNA due to the efficient neutralization; wherein the P3 buffer contains an indicator dye; and wherein the color of the cleared bacterial lysate changes upon adding the P3 buffer resulting from the decrease in pH indicating the P3 buffer was effective in causing efficient neutralization;
   (d) removing cellular debris from the cleared bacterial lysate by filtering or centrifuging to obtain a lysate filtrate, and then adsorbing the plasmid DNA in the lysate by passing the lysate filtrate over a DNA binding matrix whereby the indicator dye or dyes in the colored cleared lysate passes or pass through the DNA binding matrix being discarded as part of the waste flow through;
   (e) washing the adsorbed plasmid DNA on the DNA binding matrix by adding wash buffer and filtering or centrifuging to obtain a clear flow through of wash buffer, discarding the clear flow through wash buffer, and;
   (f) eluting the plasmid DNA from the DNA binding matrix by adding an elution buffer and filtering or centrifuging to obtain a plasmid DNA containing eluate.

12. The method of claim 11 wherein the indicator dyes or other similar dyes are selected from the group consisting of: phenol red; chloro phenol red; emerald green; methyl red; methyl green; thymol blue; bromo thymol blue; o-cresolphthalein; meta cresol purple; thymolphthalein; phenolphthalein; titan yellow; xylene cyanol; methyl orange; neutral red; cresol red; bromo cresol blue; bromo cresol green; bromo cresol purple; methylene blue; bromo phenol blue; indigo carmine; and resazurin.

13. The method of claim 11 wherein each of the buffers P1, P2, and P3 contain the same indicator dye.

14. The method of claim 11 wherein each of the buffers P1, P2, and P3 contain a different indicator dye.

15. The method of claim 11 further comprising deletion of the step where the P1 buffer is added, and wherein the bacterial cells to be lysed are added directly to the P2 buffer as the initial process step, and wherein the indicator(s) in the P2 and P3 buffers display a color change or changes in the pH range of about 6.0 to about 8.5.

16. The method of claim 11 wherein the DNA binding matrix is silica based.

17. The method of claim 11 wherein the buffers P1, P2, or P3 each further comprises an additional indicator dye or other similar dye.

18. A method for isolating plasmid DNA from bacteria via alkaline lysis, the method comprising:
(a) suspending bacterial cells in a P1 buffer with a pH of about 8, optionally containing lysozyme and RNAse A, wherein the P1 buffer contains phenol red and is red in color, a color which changes to a light shade of red to pink upon suspension of the bacterial cells;
(b) adding a sufficient amount of P2 buffer with a pH of about 11 to the bacterial suspension, wherein the P2 buffer contains emerald green and at pH 11 is blue in color, whereby adding and mixing of the P2 buffer with the bacterial suspension results in an efficient lysis to produce a bacterial lysate, wherein a visible color change from a light shade of red to pink to a deep red is caused by the increase in pH and presence of the indicator dye emerald green; and when the deep red colored bacterial lysate clarifies this is an indication that lysis of the bacterial suspension is complete and that the P2 buffer has been effective in causing efficient lysis;
(c) adding a sufficient amount of pH 3 to 6 P3 neutralization buffer to cause cellular debris precipitation, wherein the P3 buffer optionally containing RNAse A, and wherein the yellow colored acidic P3 buffer contains phenol red, thereby permitting monitoring the degree of neutralization of the bacterial lysate, and whereby adding the P3 buffer to the red bacterial lysate produces a clear yellow bacterial lysate containing increased amounts plasmid DNA in solution due to efficient and complete neutralization;
(d) removing cellular debris from the alkaline lysate by filtering or centrifuging to obtain a clear lysate filtrate, and then adsorbing the plasmid DNA in the lysate by passing the lysate filtrate over a DNA binding matrix, whereby the phenol red and emerald green in the cleared lysate pass through the DNA binding matrix and are discarded as part of the waste flow through;
(e) washing the adsorbed plasmid DNA on the DNA binding matrix by adding wash buffer and filtering or centrifuging to obtain a clear flow through of wash buffer, discarding the clear flow through wash buffer, and;
(f) eluting the plasmid DNA from the DNA binding matrix by adding an elution buffer and filtering or centrifuging to obtain a plasmid DNA containing eluate.

19. The method of claim 18 further comprising; substituting emerald green dye in the P2 buffer with phenol red dye, wherein the P2 buffer is consequently pink instead of blue, and wherein the bacterial lysate produced is therefore also pink in color.

20. A method for isolating plasmid DNA from bacteria via alkaline lysis, the method comprising:
suspending the bacteria cells in a sufficient amount of a P1 buffer of pH between 7-9, optionally containing lysozyme and RNAse A, to produce a bacterial suspension;
adding a sufficient amount of a P2 buffer of pH between 11-14 to lyse the bacteria cells producing a bacterial lysate;
adding a sufficient amount of a P3 buffer of pH between 3-5, optionally containing RNAse A, to neutralize the bacterial lysate precipitating cellular debris producing a cleared bacterial lysate containing plasmid DNA in solution;
removing the cellular debris from the cleared alkaline lysate by centrifuging or filtering to obtain a lysate filtrate;
adsorbing the plasmid DNA in the lysate filtrate to a DNA binding matrix;
washing and eluting the plasmid DNA to produce a plasmid DNA-containing eluate;
wherein the improvement comprises:
adding a sufficient amount of an indicator dye into the P1, P2, and P3 buffers such that the sequential adding of the buffers can be monitored to avoid buffer addition errors by observation of color and color changes provided by the presence of the indicator dye(s) in the P1, P2, and P3 buffers thereby providing a basis for elimination of errors associated with sample handling when adding the P1, P2, and P3 buffers;
wherein the adding of the P1 buffer produces a colored bacterial suspension aiding the monitoring of the suspension of the bacteria in view of increased contrast of the colored bacterial suspension;
wherein the adding and mixing of the P2 buffer produces a change in color of the indicator dye(s) due to the increase in pH, which pH is shifted from 0.5 to 1.0 pH units from the original pH of the P2 buffer thereby allowing the visual monitoring of the degree of lysis, because the bacterial lysate both changes color and clarifies as lysis moves to completion;
wherein the adding of the P3 buffer produces another change in color due to the decrease in pH to a pH from 0.5 to 1.5 units from the pH of the original P3 buffer, thereby allowing for the visual monitoring of the degree of neutralization and the precipitation of cellular debris to produce a more efficiently and completely neutralized cleared bacterial lysate, and therefore more frequently generating a greater amount of plasmid DNA in solution in the cleared bacterial lysate; and
wherein all indicator dye(s) are removed in the flow through as a result of the cleared bacterial lysate passing through the DNA binding matrix as part of the waste flow through caused by the elution buffer.

21. The method of claim 20 wherein the indicator dye or other similar dye in buffers P1, P2, and P3 is the same indicator dye.

22. The method of claim 21 wherein the indicator dye or other similar dye is phenol red.

23. The method of claim 20 wherein the sole indicator dye or other similar dye has a transition pH range of color change of between a pH of 4 to 9.

24. The method of claim 20 wherein the sole indicator dye or other similar dye has a transition pH range of color change of between a pH of 6 to 10.

25. A method for isolating plasmid DNA from bacteria via alkaline lysis, the method comprising:

mixing bacterial cells with a sufficient amount of a P2 buffer of pH between 11-14, to produce a bacterial-buffer suspension to produce a bacterial lysate;

adding amount of a P3 buffer of pH between 3-5, optionally containing RNAse A, sufficient to neutralize the bacterial lysate and cause the precipitation of cellular debris to produce a cleared bacterial lysate containing plasmid DNA in solution;

removing the cellular debris from the cleared alkaline lysate by centrifugation or filtration to obtain a lysate filtrate;

adsorbing the plasmid DNA in the lysate filtrate to a DNA binding matrix;

and then washing and eluting the plasmid DNA from the binding matrix to produce a plasmid DNA-containing eluate; wherein the improvement comprises:

adding a sufficient amount of an indicator dye or other similar dye into the P2, and P3 buffers such that the mixing of the bacterial cells with the P2 buffer, wherein the addition of the P3 buffer to the bacterial lysate can be monitored to avoid buffer addition errors by observation of from color and color changes caused by the presence of the indicator dye(s) in the P2, and P3 buffers thereby providing a basis for elimination of errors associated with sample handling;

wherein the mixing of the bacterial cells to the P2 buffer, results in a colored bacterial suspension that changes color and clarifies as the lysis becomes complete allowing visual monitoring of the completeness of the lysis;

wherein the adding of the P3 buffer results in a change in color due to the decrease in pH of from 0.5 to 1.5 pH units from the original P3 buffer pH, and allows for the visual monitoring of the degree of neutralization by following the changes in color and the precipitation of cellular debris during the generation of a more completely neutralized and cleared bacterial lysate, and thereby optimizing the amount of plasmid DNA present in solution in the cleared bacterial lysate; and wherein the indicator dyes are removed during the passage of the cleared bacterial lysate through the DNA binding matrix and appear as part of the waste flow through in the elution step.

26. The method of claim 25 wherein the indicator dye selected for in buffers P2, and P3 is the same indicator dye.

27. The method of claim 26 wherein the indicator dye is phenol red.

28. The method of claim 25 wherein the sole indicator dye has a transition pH range for color change between a pH of 4 to 9.

29. The method of claim 25 wherein the sole indicator dye has a transition pH range of color change between a pH of 6 to 10.

* * * * *

SEQUENCE LISTING

```
<160> NUMBER OF SEQ ID NOS: 1

<210> SEQ ID NO 1
<211> LENGTH: 199
<212> TYPE: DNA
<213> ORGANISM: Saccharomyces cerevisiae
<220> FEATURE:
<221> NAME/KEY: rep_origin
<222> LOCATION: (1)..(199)

<400> SEQUENCE: 1
```

-continued

```
tccacagaat cagggataa cgcaggaaag aacatgtgag caaaaggcgg ctccgccccc      60
cctgacgagc atcacaaaaa tcgacgctca agtcagaagc tccctcgtgc gctctcctgt    120
tccgaccctg ccgcttaccg gatacctgta ggtatctcag ttcggtgtag gtcgttcgct    180
ccaagctggg ctgtgtgca                                                 199
```